United States Patent [19]

Borody

[11] Patent Number: 5,274,001

[45] Date of Patent: Dec. 28, 1993

[54] ORTHOSTATIC LAVAGE SOLUTIONS

[76] Inventor: Thomas J. Borody, 144 Great North Rd., Five Dock, Australia

[21] Appl. No.: 536,624

[22] PCT Filed: Dec. 20, 1988

[86] PCT No.: PCT/AU88/00484

§ 371 Date: Jul. 17, 1990

§ 102(e) Date: Jul. 17, 1990

[87] PCT Pub. No.: WO87/00754

PCT Pub. Date: Feb. 12, 1987

[30] Foreign Application Priority Data

Dec. 24, 1987 [AU] Australia ................... 6088

[51] Int. Cl.$^5$ .............................. A61K 31/34
[52] U.S. Cl. .............................. 514/474; 514/892
[58] Field of Search .......................... 514/474, 892

[56] References Cited

U.S. PATENT DOCUMENTS 3,211,614 10/1965 Tumbring et al. ............... 514/474
4,705,804 10/1987 Geho et al. ..................... 514/474

FOREIGN PATENT DOCUMENTS 73343 2/1982 Australia.
305048 1/1985 Australia.
13063 9/1988 Australia.
2336922 7/1977 France.
00754 2/1987 PCT Int'l Appl..
8808715 11/1988 PCT Int'l Appl..

OTHER PUBLICATIONS

Davis, Glenn R., et al., Gastroenterology 78, 991-995 (1980).
The Merck Index, 11th edition, pp. 130-131 (1989).
Goodman and Gilman's The Pharmalogical Basis of Therapeutics, 7th ed., pp. 997-998, MacMillan, 1985.
Extra Pharmacopoeia, Martindale, 25th ed., pp. 144-147 (1967).
Patent Abstracts of Japan, C-20, p. 338, JP 59-81648, Nov. 1985.
Basu, T. K., et al., Vitamin C in Health and Diseases, Avi Publishing, pp. 135, 136, 142 (1982).
Goldsmith, G. A., J. Am. Med. Assoc., 216, No. 2, p. 337 (Apr. 12, 1971).
Hume, R., et al., J. Am. Med. Assoc. 219, No. 11, p. 1479 (Mar. 13, 1972).
Regnier, E., Review of Allergy, vol. 22, 835-846 and 948-956, Sep. 1968.
Basu, et al., "Vitamin C in Health and Disease", (Textbook), 1982, pp. 93-95, 117 & 118.

Primary Examiner—Leonard Schenkman

[57] ABSTRACT

The present invention relates to orthostatic lavage solutions or colon evacuants for cleansing the gastrointestinal tract, or for treatment of bowel diseases and/or disorders, containing an effective amount of ascorbic acid or a salt thereof.

2 Claims, No Drawings

ORTHOSTATIC LAVAGE SOLUTIONS

TECHNICAL FIELD

The present invention relates to orthostatic lavage solutions or colon evacuants for cleansing the gastrointestinal tract, or for treatment of bowel diseases and/or disorders.

BACKGROUND ART

Orthostatic lavage solutions or colon evacuants for cleansing the gastrointestinal tract were introduced into medical practice only within the last five years. The available solutions which seek to produce volumogenic diarrhoea by ingestion of relatively large volumes of electrolyte solution are almost all identical in their contents of salts, formulated so that they are relatively isotonic, and include poorly absorbable polyethylene glycol. Solutions which are commonly employed include 0.9% sodium chloride, balanced electrolyte solutions, lactated Ringers, mannitol and polyethylene glycol containing electrolyte solutions.

These solutions induce copious diarrhoea when the volume of the solution is greater than the bowel's capacity to distend and absorb it. Generally about 4 to 5 litre of the solution is necessary to obtain adequate cleansing of the gastrointestinal tract for colonoscopy or bowel surgery. Apart from the necessary diarrhoeagenic effect the large volume required and the particularly unpleasant taste of the solutions contribute to the chief side effects of nausea and vomiting. These side effects are counter productive in reaching the desired aim of complete and rapid purging and cleansing of the bowel. The unpalatability of the solutions also result in poor patient compliance.

Flavouring the currently used solution with standard agents is difficult due to the large destabilizing amount of flavouring agents required to block the unpleasant nauseating taste of salts. Sugar based flavours are not acceptable since delivery of unabsorbed sugars to the colon provides a substrate for bacteria to elaborate explosive gases such as hydrogen and methane. In fact, recent studies (J. Crowe et al.[1]) have indicated that even the unflavoured polyethylene glycol solutions currently in use may create hydrogen and methane in potentially explosive concentrations when cautery is used within the colon.

Furthermore, most bowel preparations using orthostatic lavage precede either colonoscopy or bowel surgery with a lesser usage in barium-enema bowel radiology. Since patients requiring such procedures are usually in the older age group and may be candidates for surgery after discovery of a bowel cancer, for example, it would be of advantage if the solution had bactericidal properties and/or could simultaneously replace nutrients necessary for repair.

Therefore it would be desirable to provide a colon evacuant wherein the unpleasant taste of the normally used isotonic solutions containing PEG is masked, wherein it has endogenous diarrhoea producing properties, and wherein it confers bacteriostatic of bactericidal properties to reduce bowel gas production or post-operative infection and yet can replace some nutrient value pre-operatively.

It is an object of the present invention to provide an agent which may be combined with flavouring and sweetening agents, which significantly reduces the potential for explosion due to a reduction of explosive gasses secondary to a bacteriostatic effect on bowel bacteria, and which allows a reduction in the volume of standard lavage solutions containing polyethylene glycol by at least about 25%.

Thus providing a more palatable and effective formulation, with fewer side effects, greater patient compliance and less risk of explosion.

DISCLOSURE OF THE INVENTION

The present invention provides a formulation for colon evacuation or for treatment of bowel diseases and/or disorders characterized in that it contains ascorbic acid or a salt thereof. Because of the poor stability of ascorbic acid in solution, it should be packaged separately from the other components of the formulation or coated in dry formulations. In liquid formulations, it should not be added until just before use.

The formulations of the present invention may also contain electrolytes, for example, those having an isotonic profile. The formulations may also contain sweetening and/or flavouring agents.

If uncoated ascorbic acid is employed in the formulations of the invention it can cross react in the dry form with other components of the formulation.

The present inventor has found that the addition of ascorbic acid in larger than usual doses to typical lavage solutions tends to reduce the required volume for satisfactory colon evacuation. With the typical polyethylene glycol electrolyte lavage solutions, the required volume for appropriate colon preparation is about 4 litre. The addition of ascorbic acid to the lavage solution has been shown to reduce the required volume to about 3 litre or less.

The present invention also provides a method of whole bowel irrigation wherein a volume of about 2 to 3.5 litre of a lavage solution of the present invention is administered over a period of time to induce volumogenic diarrhoea. Generally this period of time will be about 1.5 to 4 hours.

BEST MODES OF CARRYING OUT THE INVENTION

In the preferred formulations of the present invention, ascorbic acid is incorporated in larger than usual oral concentrations to give a composition in the lavage solution of between about 0.25 to 50 g/l, especially 1 to 25 g/l for colon evacuants or 20 to 35 g/l for treatment of bowel diseases and/or disorders. Since only a single dose is given during the lavage and the human intestine is capable of absorbing at most about 3 g of ascorbic acid (Hornig D. et al.[2]), the remainder of the dose contributes to the diarrhoea and inhibits bacterial gas generation and reproduction. The excess ascorbic acid is passed without doing harm to the patient whilst the absorbed quantity is available as a specific nutrient and could be advantageous in the post-operative healing stage.

Typically, lavage solutions are provided in powdered form which are reconstituted to the required volume immediately prior to use. The lavage solutions of the present invention when made up ready for use will generally contain at least about 0.25 g/l ascorbic acid. More preferably they will contain from 5 to 50 g per 3 litre of solution when made up, more preferably about 20g per 3 litre when made up.

For dry formulations the ascorbic acid must be coated. Silicone or ethyl cellulose form suitable coatings to prevent reaction between the ascorbic acid and other components of the formulation.

Suitable coated ascorbic acid is available from Roche Products Pty Ltd as Coated Ascorbic Acid, Type EC and Coated Ascorbic Acid, Type SC.

Preferred lavage solutions of the present invention also contain high molecular weight polyethylene glycol such as polyethylene glycol having molecular weights greater than about 2000. Preferred polyethylene glycol has a molecular weight of about 3000 to 4500 such as PEG 3350, or PEG 4000.

Preferred lavage solutions of the present invention also contain a number of electrolytes and preferably have an isotonic electrolyte profile.

Preferred solutions have the following constituents in the range as specified.

|  | RANGE OF CONCENTRATION g/liter $H_2O$ of made up solution |
| --- | --- |
| Polyethylene glycol | 30–60 |
| Sodium chloride | 0.5–3.0 |
| Potassium chloride | 0.2–2.0 |
| Sodium hydrogen carbonate | 0.5–5.0 |
| Sodium sulfate (anhydrous) | 2.0–10.0 |
| Ascorbic acid | 0.25–50.0 |

Preferably, the polyethylene glycol in the standard lavage solutions is adjusted so as to result in an osmolality of approximately 289 m osm/litre.

It is also possible to add flavourings to the lavage solutions of the present invention so long as these flavourings are not metabolized to an explosive gas such as hydrogen or methane in the bowel. For example aspartame may be added in a concentration of about 0.05 to 1%. Lemon flavour (SD - Natural lemon powder flavour No. 12606) or pineapple flavour (10966) may also be added at concentrations of 0.5 to 4.0% or cyclamates may be added to increase the palatability of the lavage solution.

The lavage solutions of the present invention are also useful in the treatment of certain gastrointestinal conditions such as small bowel bacterial overgrowth and irritable bowel syndrome as well as useful in treating acute or chronic bacterial bowel infections, for example, infection of the bowel with one or more bacteria including *Campylobacter jejuni, Yersinia enterocolitica, Clostridium difficile, Cryptosporidium isospore belli*. The lavage solutions of the present invention can also be used in the treatment of chronic inflammatory bowel disease such as Crohns disease or ulcerative colitis. In treating these conditions, ascorbic acid or its salts is used in a wide range of concentrations depending on the specific condition and may vary from about 1 g to about 50 g per litre, preferably from 20 g to 35 g per litre. Therefore, the lavage solutions useful in methods to treat the acute or chronic bacterial bowel infections or chronic inflammatory bowel disease will contain ascorbic acids or a salt thereof in a range so that when made up as ready for ingestion, the concentration of ascorbic acid will be from about 1 to 50 g per litre. These lavage solutions useful in these treatments will also preferably be isotonic and include high molecular weight polyethylene glycol.

The invention will further be described by reference to the following examples.

EXAMPLE 1

A solution having the following composition was made up:

|  | g/L Water |
| --- | --- |
| Polyethylene glycol | 54 |
| Sodium chloride | 1.46 |
| Potassium chloride | 0.745 |
| Sodium hydrogen carbonate | 1.68 |
| Sodium sulfate | 5.68 |
| Ascorbic acid | 6.6 |

A total of 3 litre was administered to the patient over 2 to 5 hours and the bowel preparation quality was found to be comparable to that requiring 4 litre of the standard available preparation. Ingestion was greatly facilitated due to the pleasant acidic taste which masked the usual nauseating taste of the salty polyethylene glycol solution. Colon hydrogen levels were acceptably low. Biopsies of colon obtained from the ascending transverse and descending colon sites were normal and without mucosal oedema.

EXAMPLE 2

A solution having the following composition was made up and administered in Example 1.

|  | g/L Water |
| --- | --- |
| Polyethylene glycol | 38 |
| Sodium chloride | 0.95 |
| Potassium chloride | 1.63 |
| Sodium hydrogen carbonate | 3.42 |
| Sodium sulfate | 2.75 |
| Ascorbic acid | 25 |
| Lemon flavour | 7.5 |

EXAMPLE 3

A solution having the following composition was made up and administered as in Example 1.

|  | g/L Water |
| --- | --- |
| Polyethylene glycol | 49 |
| Sodium chloride | 2.4 |
| Potassium chloride | 1.2 |
| Sodium hydrogen carbonate | 2.82 |
| Sodium sulfate | 7.41 |
| Ascorbic acid | 37.1 |
| Pineapple flavour | 9.0 |

EXAMPLE 4

A solution having the following composition was made up and administered as in Example 1.

|  | g/L Water |
| --- | --- |
| Polyethylene glycol | 32 |
| Sodium chloride | 0.6 |
| Potassium chloride | 0.23 |
| Sodium hydrogen carbonate | 0.65 |
| Sodium sulfate | 2.25 |
| Ascorbic acid | 0.8 |
| Cyclamate | 0.5 |

EXAMPLE 5

A solution having the following composition was made up and administered as in Example 1.

|  | g/L Water |
|---|---|
| Polyethylene glycol | 57 |
| Sodium chloride | 2.7 |
| Potassium chloride | 1.8 |
| Sodium hydrogen carbonate | 4.45 |
| Sodium sulfate | 9.5 |
| Ascorbic acid | 46.5 |
| Aspartame | 9.0 |

EXAMPLE 6

A dry formulation having the following composition was made up:

| Potassium chloride | 2.092 Kg |
|---|---|
| Sodium chloride | 4.127 |
| Sodium hydrogen carbonate | 4.748 |
| Sodium sulphate (Anhydrous) | 16.054 |
| Ascorbic acid (Silicone coated) | 16.959 |
| Lemon flavour 12606 | 2.826 |
| Aspartame | .565 |
| Polyethylene glycol 4000 | 152.629 |
| Total | 200.000 |

EXAMPLE 7

A dry formulation having the following composition was made up:

| Potassium chloride | 2.092 Kg |
|---|---|
| Sodium chloride | 4.127 |
| Sodium hydrogen carbonate | 4.748 |
| Sodium sulfate (Anhydrous) | 16.054 |
| Ascorbic acid (Silicone coated) | 16.959 |

-continued

| Pineapple flavour 10966 | 1.979 |
|---|---|
| Aspartame | .565 |
| Polyethylene glycol 4000 | 152.629 |
| Total | 199.153 |

Individual doses of the dry formulations were made up to a volume of 3 litre with water, and the resultant solution was kept cold to increase palatability. The solution was administered to the patient over a period of 1 to 5 hours.

The formulation may be packaged for single applications in sachets, plastic bags or in a 3–4 litre jug to which water may be added to be made up to a specific volume. Alternatively the formulation may be packaged in screw top boxes or cartons, preferably with an air tight seal. Vitamin C can be kept separately in an air tight sachet to be added at the time of mixing particularly if it is uncoated by ethyl cellulose or silicone. It can also be packaged in sachets lined by agents such as Mylar to prevent water absorption.

REFERENCES

1. J. Crowe et al.; A Study of Intracolonic Hydrogen and Methane Concentrations in Patients. GUT 1987; 28: A1370.
2. Hornig D. et al.; Int. J. Vit. Nutr. Res. 1980; 50: 309.

I claim:

1. A method of whole bowel irrigation in a patient requiring such irrigation, consisting of the step of administering orally to said patient a volume of about 2 to 3.5 liters of a bacteriostatic or bacteriocidal formulation over a period of time to induce volumogenic diarrhoea, said formulation consisting essentially of 30 to 60 g/l of high molecular weight polyethylene glycol, 0.2 to 20 g/l of at least one electrolyte having at least one alkali metal salt and 0.25 to 50 g/l of ascorbic acid or a salt thereof.

2. A method according to claim 1 wherein the formulation is administered over about 1.5 to 4 hours.

* * * * *